United States Patent
Ahan et al.

(10) Patent No.: US 11,707,697 B2
(45) Date of Patent: Jul. 25, 2023

(54) DIVIDING WALL DISTILLATION COLUMN AND METHOD FOR REFINING VINYLIDENE DICHLORIDE BY USING SAME

(71) Applicant: Hanwha Solutions Corporation, Seoul (KR)

(72) Inventors: Woo Youl Ahan, Daejeon (KR); Shin Beom Lee, Daejeon (KR)

(73) Assignee: Hanwha Solutions Corporation, Seoul (KR)

( * ) Notice: Subject to any disclaimer, the term of this patent is extended or adjusted under 35 U.S.C. 154(b) by 0 days.

(21) Appl. No.: 17/541,418

(22) Filed: Dec. 3, 2021

(65) Prior Publication Data
US 2022/0088502 A1 Mar. 24, 2022

Related U.S. Application Data

(62) Division of application No. 16/649,704, filed as application No. PCT/KR2018/010832 on Sep. 14, 2018, now Pat. No. 11,219,840.

(30) Foreign Application Priority Data

Sep. 25, 2017 (KR) .................. 10-2017-0123726

(51) Int. Cl.
*B01D 3/14* (2006.01)
*C07C 17/383* (2006.01)
*C07C 21/08* (2006.01)

(52) U.S. Cl.
CPC ............ *B01D 3/141* (2013.01); *C07C 17/383* (2013.01); *C07C 21/08* (2013.01)

(58) Field of Classification Search
CPC ........ B01D 3/14; B01D 3/141; C07C 17/383; C07C 17/386; C07C 21/08
See application file for complete search history.

(56) References Cited

U.S. PATENT DOCUMENTS 3,304,337 A * 2/1967 Jordan, Jr. .............. C07C 17/10
570/255
11,219,840 B2 * 1/2022 Ahan ...................... C07C 21/08
(Continued)

FOREIGN PATENT DOCUMENTS

| CN | 1299296 | 6/2001 |
| CN | 102659508 | 9/2012 |

(Continued)

OTHER PUBLICATIONS

Norbert Asprion, Gerd Kaibel, "Dividing wall columns: Fundamentals and recent advances", Chemical Engineering and Processing: Process Intensification, vol. 49, Issue 2, 2010, pp. 139-146, ISSN 0255-2701, https://doi.org/10.1016/j.cep.2010.01.013.*
Norbert Asprion et al., "Dividing wall columns: Fundamentals and recent advances", Chemical Engineering and Processing: Process Intensification, vol. 49, No. 2, pp. 139-146.
KIPO, PCT Search Report & Written Opinion of PCT/KR2018/010832 dated Dec. 19, 2018.
(Continued)

*Primary Examiner* — Jonathan Luke Pilcher
(74) *Attorney, Agent, or Firm* — Lex IP Meister, PLLC (57) ABSTRACT

The present disclosure relates to a dividing wall distillation column and a method for refining vinylidene dichloride by using the same and, more specifically, to a dividing wall distillation column capable of refining, in a high purity, vinylidene dichloride from a crude product; and a method for refining vinylidene dichloride by using the same. According to the dividing wall distillation column of the present disclosure and the method for refining vinylidene dichloride by using the same, vinylidene dichloride can be refined, in a high purity, from a crude product having a small amount of vinylidene dichloride and a large quantity of high boiling components, and energy consumption can be reduced more than that in conventional cases.

5 Claims, 2 Drawing Sheets

(56) References Cited

U.S. PATENT DOCUMENTS

| | | |
|---|---|---|
| 2003/0047438 A1 | 3/2003 | Tamura et al. |
| 2004/0045804 A1 | 3/2004 | Bohner et al. |
| 2011/0139604 A1 | 6/2011 | Burst et al. |
| 2012/0006673 A1 | 1/2012 | Lee et al. |
| 2014/0371488 A1 | 12/2014 | Lee et al. |

FOREIGN PATENT DOCUMENTS

| | | |
|---|---|---|
| CN | 103170150 | 6/2013 |
| CN | 103418152 | 12/2013 |
| CN | 103432761 | 12/2013 |
| EP | 1084741 | 3/2001 |
| JP | 2013-244464 | 12/2013 |
| KR | 10-0795650 | 6/2003 |
| KR | 10-1165371 | 7/2012 |
| WO | 2005-037769 | 4/2005 |
| WO | 2013-0182499 | 12/2013 |

OTHER PUBLICATIONS

Norbert Asprion et al., "Dividing wall columns: Fundamentals and recent advances", Chemical Engineering and Processing 49 (2010) 139-146.

Nguyen Van Duc Long et al., "A novel self-heat recuperative dividing wall column to maximize energy efficiency and column throughput in retrofitting and debottlenecking of a side stream column", Applied Energy 159 (2015) 28-38.

Ben-Guang Rong, "Synthesis of dividing-wall columns (DWC) for multicomponent distillations—A systematic approach", Chemical, Engineering Research and Design, vol. 89, No. 8, pp. 1281-1294.

A. A. Kiss et al., "Efficient bioethanol dehydration in azeotropic and extractive dividing-wall columns", Procedia Engineering vol. 42, pp. 566-572.

Anton A. Kiss et al., "A control perspective on process intensification in dividing-wall columns", Chemical Engineering and Processing 50 (2011) 281-292.

* cited by examiner

DIVIDING WALL DISTILLATION COLUMN AND METHOD FOR REFINING VINYLIDENE DICHLORIDE BY USING SAME

CROSS-REFERENCE TO RELATED APPLICATION(S)

This application is a Divisional Application of U.S. patent application Ser. No. 16/649,704, which was filed on Mar. 23, 2020, which claims priority to or the benefit of PCT/KR2018/010832 filed on Sep. 14, 2018 and Korean Patent Application No. 10-2017-0123726 filed on Sep. 25, 2017 with the Korean Intellectual Property Office, the disclosure of which is incorporated herein by reference in its entirety.

BACKGROUND OF THE INVENTION

(a) Field of the Invention

The present disclosure relates to a dividing wall distillation column and a method for refining vinylidene dichloride by using the same, and more particularly, to a dividing wall distillation column capable of refining, in a high purity, vinylidene dichloride from a crude product containing vinylidene dichloride; and a method for refining vinylidene dichloride by using the same.

(b) Description of the Related Art

Vinylidene dichloride is a compound used in the manufacture of semiconductor equipment and in the manufacture of polyvinylidene dichloride copolymer, and since two hydrogens bonded to the same carbon in ethylene are substituted by chlorine, it may also be referred to as 1,1-dichloroethylene or sometimes abbreviated as VDC.

Meanwhile, vinylidene dichloride is prepared by adding chlorine to vinyl chloride to produce $CH_2Cl-CHCl_2$, from which hydrogen chloride is removed with a lime oil, and in this process, it is recovered in the form of a mixture containing impurities such as cis- and trans-isomers of chloroacetylene and 1,2-dichloroethene, which are formed by side reactions.

However, impurities can cause problems in the application of products to which vinylidene dichloride is applied, and in particular, since chloroacetylene is toxic and explosive, there is a demand for the production of ultra-high purity vinylidene dichloride hardly containing impurities.

Thus, a fractional distillation column process that can be separated by using a difference in the boiling points of the compounds is generally used, and in particular, a continuous two-column distillation system in which a mixture can be accurately separated from each distillation column while passing through a plurality of distillation columns is used for the refinement of vinylidene dichloride.

Figure 1:
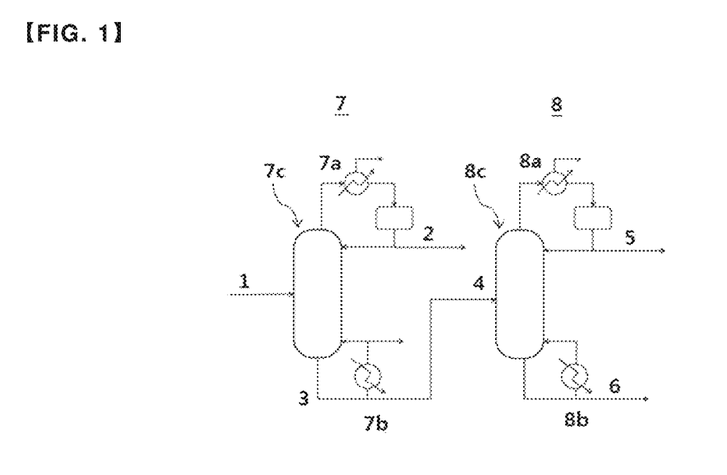
FIG. 1 is a view showing two continuous distillation columns of the prior art.

In this regard, FIG. 1 shows a schematic diagram of two continuous distillation columns of the prior art.

Referring to FIG. 1, the dividing wall column includes two distillation columns 7 and 8 each including condensers 7a and 8a, reboilers 7b and 8b and main columns 7c and 8c, wherein a mixture stream 1 fed to a first distillation column 7 is primarily divided into a low boiling component 2 and a high boiling component 3.

The high boiling component 3 discharged to the lower part of the first distillation column 7 secondarily continuously flows into a second distillation column 8. The high boiling component 4 fed to the second distillation column 8 is finally divided again into a low boiling component 5 and a high boiling component 6, where they are discharged.

However, when two continuous distillation columns are used, a relatively large amount of energy is required for the operation of a plurality of fractional distillation columns, and therefore, there is a disadvantage that it is not economical. In addition to this, there is a problem that the thermodynamic efficiency is lowered due to the remixing of the middle boiling material in the first distillation column 7.

Meanwhile, in the case of vinylidene dichloride, since it is a monomer that is easily polymerized as well known, the longer the residence time in the distillation column, the higher the possibility of polymerization. In the two continuous distillation columns according to FIG. 1, since the residence time of vinylidene dichloride is relatively long, a part thereof may be polymerized in the distillation process, in particular when fed to the second distillation column 8, it can be polymerized.

Therefore, there is a high need for a technology capable of stably separating desired high-purity vinylidene dichloride while improving energy efficiency.

SUMMARY OF THE INVENTION

It is an object of the present disclosure to provide a dividing wall distillation column capable of efficiently separating a crude product containing vinylidene dichloride, and a method for refining vinylidene dichloride by using the same.

In one aspect of the present disclosure for achieving the above object, there is provided a dividing wall distillation column for the fractional distillation of a crude product containing vinylidene dichloride (1,1-dichloroethylene), the dividing wall distillation column comprising: a main column having a dividing wall, a condenser, and a reboiler, wherein the main column includes, based on a vertical cross section, a feed zone and an outflow zone partitioned on one side and the other side, with the dividing wall being interposed therebetween, a column top zone adjacent to the upper end of the dividing wall and a column bottom zone adjacent to the lower end, wherein the dividing wall is divided into a first stream falling through the feed zone and a second stream falling through the outflow zone, when a liquid stream condensed in the column top zone falls to the column bottom zone, and wherein at least a part of the dividing wall is deflected in the direction of the feed zone so that a quantitative ratio of the first stream to the second stream satisfies the following Equation 1.

$$N1/(N1+N2)=X \tag{1}$$

wherein, N1 is the flow rate of the first stream, N2 is the flow rate of the second stream, and X is 0.2 to 0.5, specifically 0.3 to 0.4, more specifically 0.3.

In the crude product, a low boiling component flows out of the column top zone, a high boiling component flows out of the column bottom zone, a middle boiling component flows out of the outflow zone, wherein the middle boiling component may include vinylidene dichloride as a main component.

In one specific example, based on a vertical cross section, the length of the dividing wall may be 40% to 70% relative to the length occupied by the total column plate number in the main column.

The dividing wall may also include, a first wall which is adjacent to the column top zone and is relatively adjacent to the inner wall of the feed zone on the basis of a virtual vertical plane that symmetrically partitions the main column, a second wall which is adjacent to the column bottom zone and located on the vertical plane, and.

a third wall forming a level difference in an extended form between the first wall and the second wall.

The third wall may be inclined at an angle of 20 to 60 degrees with respect to the ground.

Based on a vertical cross section, the distance between the inner wall of the feed zone and the first wall may be 30% to 70% relative to the distance between the feed zone and the second wall.

The feed zone is divided into an upper feed zone and a lower feed zone with reference to a portion where the first wall and the third wall are connected, and may be divided into an upper outflow zone and a lower outflow zone with reference to a portion where the second wall and the third wall are connected.

A feed plate into which a crude product flows is formed at a portion where the upper feed zone and the lower feed zone come into contact with each other, and an outflow plate through which a middle boiling component flows out may be formed at a portion where the upper outflow zone and the lower outflow zone come into contact with each other.

In another aspect of the present disclosure, there is provided a method for refining vinylidene dichloride comprising the step of fractionally distilling a crude product containing vinylidene dichloride using the dividing wall distillation column.

In the above step, the operating pressure of the main column may be 1 bar to 2 bar, and the content of vinylidene dichloride may be 90% by weight to 99.5% by weight with respect to the total weight of the crude product.

According to some embodiments of the present disclosure, the dividing wall distillation column provides a distillation column structure suitable for the refinement of vinylidene dichloride, and thus can be used for the refinement of vinylidene dichloride on a commercial scale with high energy efficiency.

Further, according to the refinement method of vinylidene dichloride using the dividing wall distillation column of the present disclosure, the crude product containing vinylidene dichloride can be refined into an ultra-high purity monomer having a vinylidene dichloride content of 99.9% by weight. Further, energy consumption can be reduced as compared with the case of using two continuous distillation columns of the prior art. This can contribute to an improvement in productivity in the entire refinement process of vinylidene dichloride.

DETAILED DESCRIPTION OF THE EMBODIMENTS

As used herein, terms such as first, second, and the like may be used to describe various components, and the terms are used only to discriminate one constituent element from another component.

Further, the terms used herein are used only to describe exemplary embodiments, and are not intended to limit the present disclosure. A singular expression includes a plural expression unless they have definitely opposite meanings in the context. It should be understood that the terms "comprise", "include", and "have" as used herein are intended to designate the presence of stated features, numbers, steps, constitutional elements, or combinations thereof, but it should be understood that they do not preclude a possibility of existence or addition of one or more other features, numbers, steps, constitutional elements, or combinations thereof.

Further, in the present disclosure, in case a layer or an element is mentioned to be formed "on" or "above" another layer or element, it means that the layer or element is directly formed on the other layer or element, or it means that another layer or element may be additionally formed between layers or on a subject or substrate.

Since a variety of modification may be made to the present disclosure and there may be various forms of the present disclosure, specific examples are illustrated and will be described in detail below. However, it should be understood that this is not intended to limit the present disclosure to particular forms disclosed herein, and the invention is to cover all modifications, equivalents, or alternatives falling within the spirit and technical scope of the present disclosure.

Hereinafter, the dividing wall distillation column of the present disclosure and a method for refining vinylidene dichloride using the same will be described in detail.

In one embodiment according to the present disclosure, the dividing wall distillation column is a distillation column for fractional distillation of a crude product containing vinylidene dichloride (1,1-dichloroethylene), the dividing wall distillation column including: a main column having a dividing wall, a condenser, and a reboiler, wherein the main column includes, based on a vertical cross section, a feed zone and an outflow zone partitioned on one side and the other side, with the dividing wall being interposed therebetween, a column top zone adjacent to the upper end of the dividing wall and a column bottom zone adjacent to the lower end, wherein the dividing wall is divided into a first stream falling through the feed zone and a second stream falling through the outflow zone when the liquid flow condensed in the column top zone falls to the column bottom zone, and wherein at least a part of the dividing wall is deflected in the direction of the feed zone so that a quantitative ratio of the first stream to the second stream satisfies the following Equation 1.

$$N1/(N1+N2)=X \tag{1}$$

wherein, N1 is the flow rate of the first stream, N2 is the flow rate of the second stream, and X is 0.2 to 0.5, specifically 0.3 to 0.4, more specifically 0.3.

The advantage of the dividing wall distillation column is that within one distillation column, the space divided by the dividing wall functions as two continuous distillation columns, in particular, the feed zone partitioned by the dividing wall acts as a pre-separator, so that due to the separation of the high boiling component and the low boiling component, the liquid composition substantially coincides with the equilibrium distillation curve and the remixing effect is suppressed, and thus, the thermodynamic efficiency for separation is improved.

As used herein, the "crude product" is a subject of the refinement process of the present disclosure for obtaining high-purity vinylidene dichloride as a final product, which is prepared by adding chlorine to vinyl chloride to produce $CH_2Cl-CHCl_2$, from which hydrogen chloride is removed with a lime oil, and the crude product refers to a product in an unrefined state which is prepared in the form of a mixture containing vinylidene dichloride, and impurities such as cis- and trans-isomers of chloroacetylene and 1,2-dichloroethene formed by side reactions in the above process.

The dividing wall column of the present disclosure is used for refining, in a high purity, vinylidene dichloride from the crude product.

Further, as used herein, the term "low boiling component" means a material having a boiling point lower than 31.6° C., which is the boiling point of vinylidene dichloride among the components included in the crude product containing vinylidene dichloride, and the "high boiling component" means a material having a boiling point higher than that of vinylidene dichloride among the components included in the crude product containing vinylidene dichloride. That is, vinylidene dichloride among the components contained in the crude product can be understood as a "middle boiling component".

The low boiling component may be, specifically, chloroacetylene, the middle boiling component may be, specifically, vinylidene dichloride, and the high boiling component may be cis-1,2-dichloroethene and/or trans-1,2-dichloroethene.

A low boiling component of the crude product flows out of the column top zone, a high boiling component flows out of the column bottom zone, a middle boiling component flows out of the outflow zone, wherein the middle boiling component may include vinylidene dichloride as a main component.

The middle boiling component flowing out of the outflow zone through the dividing wall distillation column of the present disclosure includes vinylidene dichloride as a main component, for example, in an amount of about 99.5% by weight or more, preferably about 99.7% by weight or more, more preferably about 99.9% by weight or more, with respect to the total weight of the middle boiling component. That is, when using the dividing wall distillation column of the present disclosure, ultra-high purity vinylidene dichloride having a purity of about 99.5% by weight or more, preferably about 99.7% by weight or more, more preferably about 99.9% by weight can be obtained.

Based on the experiments of the present inventors, it was confirmed that at the point where the liquid flow from the column top zone to the column bottom direction is divided by a dividing column, when the cross-sectional area of the feed zone is designed to be relatively small so as to satisfy the value of Equation 1, specifically, when the flow rate of the first stream falling into the feed zone is designed to be relatively less than the flow rate of the second stream falling into the outflow zone, the thermodynamic efficiency of the distillation column is more dramatically improved while significantly reducing a phenomenon in which vinylidene dichloride having a middle boiling point and cis-1,2-dichloroethane and trans-1,2-dichloroethane having a middle boiling point are re-mixed with the crude product flowing into the inflow zone. In particular, it was confirmed that the separation efficiency for the high boiling point material is excellent and the purity of the middle boiling point component flowing out to the outflow zone is obtained with a high purity reaching about 99.9% by weight.

Therefore, the advantage of the dividing wall distillation column of the present disclosure is that at least a part of the dividing wall is deflected in the direction of the feed zone, and thereby, it is easy to obtain ultra-high purity vinylidene dichloride with excellent thermodynamic efficiency.

Further, since the residence time of vinylidene dichloride in the entire distillation column is relatively reduced, the possibility of polymerization of vinylidene dichloride in the course of the distillation can be reduced.

Figure 2:
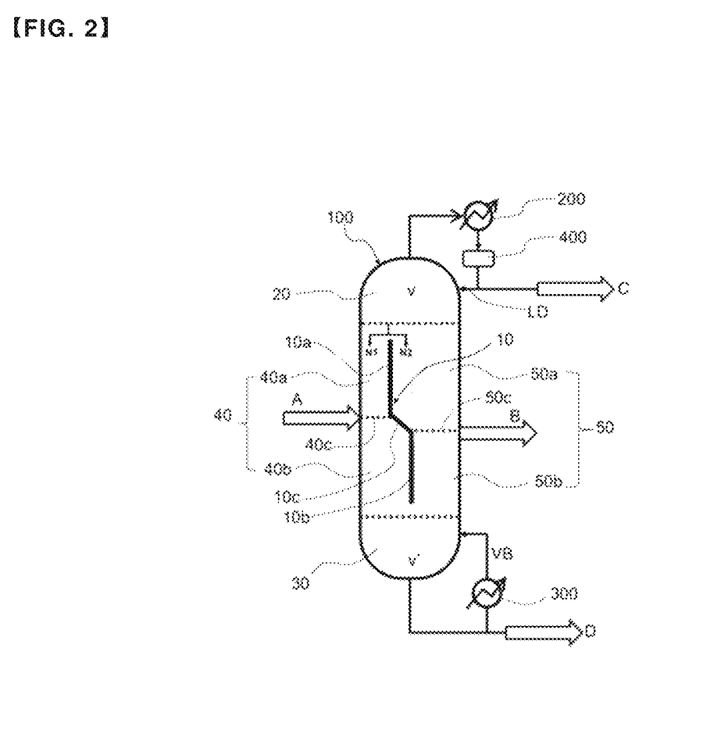
FIG. 2 is a view showing a dividing wail distillation column according to one embodiment of the present disclosure.

In this regard, the structure of a dividing wall distillation column according to one embodiment of the present disclosure is schematically illustrated in FIG. 2.

Referring to FIG. 2, the dividing wall distillation column of the present invention includes a main column 100 having a dividing wall 10, a condenser 200, and a reboiler 300, wherein the main column 100 is roughly divided into a column top zone 20, a column bottom zone 30, a feed zone 40, and an outflow zone 50.

The columns in the main column are not shown for convenience, but in the following, the term "length" refers to a length determined by the column plate number. Moreover, within one independent zone, for example, within a column top zone 20, a column bottom zone 30, an upper feed zone 40a, a lower feed zone 40b, an upper outflow zone 50a and a lower outflow zone 50b, the column plates are arranged at equal intervals, and the spacing of the column plates in the zones that are distinct from each other may be the same or different independently of each other.

The condenser 200 is a device for depriving evaporation heat of a mixture in a gaseous state and condensing the mixture, and a condenser used in a conventional chemical engineering system may be used without limitation.

The reboiler 300 is a device for providing evaporation heat to a mixture in a liquid state and evaporating the mixture, and a reboiler used in a conventional chemical engineering system may be used without limitation.

In the dividing wall distillation column, the energy consumption of the condenser 200 and the reboiler 300 varies depending on various conditions including the length and position of the main column, the specific operating conditions of the distillation column, and the composition of the incoming flow, and the total energy consumption may be evaluated by the sum of the energy consumptions of the condenser 200 and the reboiler 300. According to the dividing wall distillation column of the present disclosure and a refinement method using the same, in the case of refining the same crude product, the energy saving rate can be remarkably reduced by about 10 to about 30% as compared to the two continuous distillation columns of the prior art.

The main column 100 may be roughly divided into four zones, i.e., a column top zone 20, a feed zone 40, an outflow zone 50, and a column bottom zone 30 by the dividing wall 10.

The column top zone 20 is an upper region of the dividing wall 10, and refers to an upper region of the main column 100 without the dividing wall 10.

The feed zone 40 is an region where one side is partitioned by the dividing wall 10, which is an region into which the flow of the crude product A containing vinylidene dichloride flows.

The dividing wall 10 includes a first wall 10a which is adjacent to the column top zone 20 and is relatively adjacent to the inner wall of the feed zone 40 on the basis of a virtual vertical plane (v-v') that symmetrically partitions the main column 100, a second wall 10b which is adjacent to the column bottom zone 30 and located on the vertical plane (v-v'), and a third wall 10c forming a level difference in an extended form between the first wall 10a and the second wall 10b. Therefore, the dividing wall 10 is configured such that the first wall 10a is deflected in the direction of the feed zone 40 with respect to the vertical plane v-v' of the main column 100.

During the distillation process, a liquid stream flows from the column top zone 20 in the direction of the column bottom zone 30 is generated, and the liquid stream is divided into a first stream N1 in the direction of the feed zone 40 and a second stream N2 in the direction of the outflow zone 50 with reference to the first wall 10a.

By the way, since the first wall 10a of the dividing wall has a shape deflected toward the feed zone 40, the flow rate of the second stream N2 is relatively higher than the flow rate of the first stream N1. Since most of the first stream N1 and the second stream N2 include the middle boiling component, remixing of the first stream N1 flowing into the feed zone and the incoming crude product A will cause a reduction in distillation efficiency. Therefore, in the present disclosure, due to the morphological characteristics of the dividing wall 10 having the deflected first wall 10a, remixing with the crude product A can be minimized, thereby maximizing the refinement efficiency of the middle boiling component.

However, based on the experiments of the present inventors, it was confirmed that when the dividing wall 10 is designed such that a quantitative ratio of the first stream N1 and the second stream N2 satisfies N1/(N1+N2)=0.3 to 0.4, particularly preferably 0.3, the separation efficiency is most superior. This is expected to be due to the fact that the composition of the liquid stream under the quantitative ratio according to the present disclosure most coincides with the equilibrium distillation curve.

In the above quantitative ratio, based on a vertical cross section, the distance between the inner wall of the feed zone and the first wall 10a is formed from 30% to 70% compared to the distance between the feed zone and the second wall 10b, and more specifically, it may be formed from 30% to 40%.

Since the third wall 10c can act as a kind of resistance to the gas flow rising in the feed zone and the liquid flow falling in the outflow zone, it is preferable to have a gentle slope. Thus, in the present disclosure, the third wall 10c may be inclined have a slope at an angle of 20 to 60 degrees, specifically 20 to 45 degrees, and more specifically 20 to 30 degrees with respect to the ground.

The feed zone 40 can be again divided into an upper feed zone 40a and a lower feed zone 40b. In detail, it can be divided into an upper feed zone 40a and a lower feed zone 40b with reference to a portion where the first wall 10a and the third wall 10c are connected. Further, a feed plate 40c into which the crude product A flows is formed at a portion where the upper feed zone 40a and the lower feed zone 40b come into contact with each other.

The outflow zone 50 can be divided into an upper outflow zone 50a and a lower outflow zone 50b. In detail, it can be divided into an upper outflow zone 50a and a lower outflow zone 50b with reference to a portion where the second wall 10b and the third wall 10c are connected. Further, an outflow end 50c through which the middle boiling component B flows out is formed at a portion where the upper outflow zone 50a and the lower outflow zone 50b come into contact with each other.

The upper feed zone 40a is an upper region of the feed zone 40 and is a sub-region located above the flow of the crude product A fed to the main column 100. In addition, the lower feed zone 40b is a lower region of the feed zone 40 and is a sub-region located below the flow of the crude product A fed to the main column 100.

The outflow zone 50 is an region in which one side is partitioned by the dividing wall 10, and is a zone through which the flow of the middle boiling component B containing refined high purity vinylidene dichloride is discharged. The upper outflow zone 50a is an upper region of the outflow zone 50 and is a sub-region located above the flow of the middle boiling component B discharged from the main column 100. In addition, the lower outflow zone 50b is a lower region of the outflow zone 50 and is a sub-region located below the flow of the middle boiling component B discharged from the main column 100.

The column bottom zone 30 is a lower region of the dividing wall 10 and refers to a lower region of the main column 100 without the dividing wall 10.

In the dividing wall distillation column, since the space divided by the dividing wall 10 serves as a preliminary separator, the liquid composition almost coincides with the equilibrium distillation curve due to the separation of the high boiling component and the low boiling component, and the remixing effect is suppressed, resulting in improved thermodynamic efficiency for separation.

The upper feed zone 40a and the lower feed zone 40b play a similar role to that of a preliminary separator of a conventional process. That is, the feed zone 40 including the upper feed zone 40a and the lower feed zone 40b may be referred to as a kind of preliminary separation region. The mixture flowing into the preliminary separation zone is largely separated into a low boiling component and a high boiling component. Some of the low boiling component and the high boiling component separated in the preliminary separation region flow into the column top zone 20 and the column bottom zone 30, and portions thereof flow again into the upper outflow zone 50a and the lower outflow zone 50b, where they are re-distilled.

The upper outflow zone 50a and the lower outflow zone 50b serve like a main separator of the conventional process. That is, the outflow zone 50 including the upper outflow zone 50a and the lower outflow zone 50b may be referred to as a main separation region. The low boiling component and the middle boiling component are mainly separated in the upper portion of the dividing wall 10 of the main separation region, and the middle boiling component and the high boiling component are mainly separated in the lower portion.

After the low boiling component passes through the column top zone 20 of the main column 100 and the condenser 200, a portion thereof is separated into a low boiling component C and the other portion thereof returns in the form of a liquid stream LD to the column top zone 20 of the main column 100.

After the high boiling component passes through the column bottom zone 30 the main column 100 and the reboiler 300, a portion thereof is separated into a high boiling component D, and the other portion thereof returns in the form of a vapor stream VB to the column bottom zone 30 of the main column 100.

The dividing wall distillation column of the present disclosure may further include a condenser drum 400. The condenser drum 400 is a device for giving a buffer for a stable return and feed.

Figure 3:
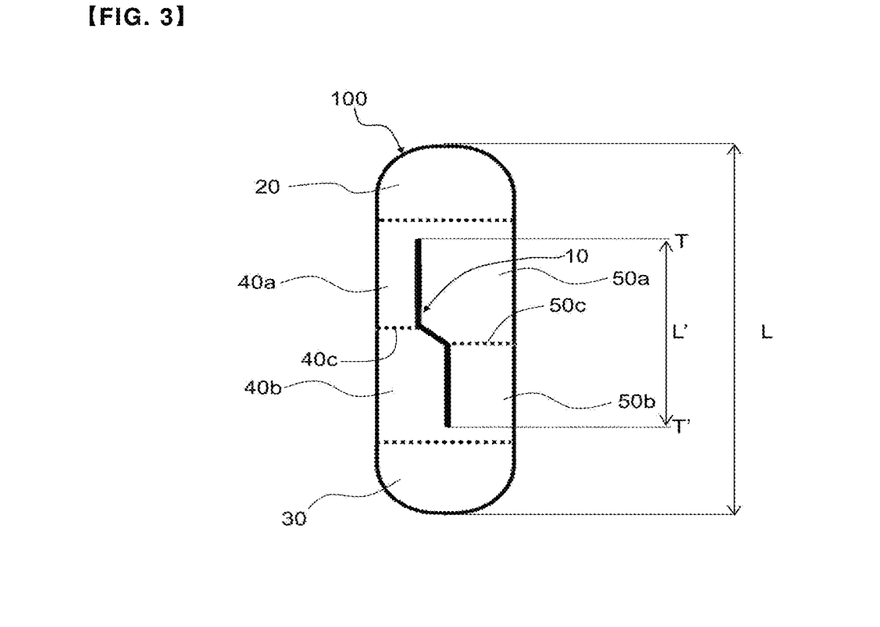
FIG. 3 is a view showing the main column of the dividing wall distillation column according to one embodiment of the present disclosure.

Referring to FIG. 3 along with FIG. 2, when the length occupied by the entire column plate number of the main column 100 is referred to as L, and the length of the dividing wall 10 is L', L' may be about 30 to about 90% of L, preferably about 40% to about 70% of L.

The position (T) at which the dividing wall 10 starts is about 20% or more from the upper end with respect to the length occupied by the entire column plate number of the main column 100, and the position T' at which the dividing wall 100 ends may be within about 90%, or about 85%, or about 80% from the upper end of the main column 100.

According to the dividing wall distillation column of the present disclosure and a refinement method using the same, when the position and length of the dividing wall are set to satisfy as described above, the energy saving efficiency is maximized, and the high boiling point component can be effectively separated.

In the dividing wall distillation column of the present disclosure, the crude product A containing vinylidene dichloride flows into the feed zone 40. More specifically, the crude product A containing vinylidene dichloride flows into a middle region of the feed zone 40, that is, a feed plate 40c where an upper feed zone 40a and a lower feed zone 40b come into contact with each other.

The low boiling component C is separated at the upper part of the dividing wall 10, the high boiling component D is separated at the lower part of the dividing wall 10, and the middle boiling component B is separated and discharged to the outflow zone 50. More specifically, the middle boiling component B flows out from a middle region of the outflow zone 50, that is, an outflow plate 50c where upper outflow zone 50a and lower outflow zone 50b come into contact with each other.

The middle boiling component B is characterized by being ultra-high purity vinylidene dichloride.

According to the present disclosure, by adjusting and optimizing the position of the main column, the length of the main column, the position of the feed plate and the position of the outflow plate as described above, even when the crude product to be refined contains a high boiling component in a high content, vinylidene dichloride can be refined in high purity of at least 99.5% by weight with low energy consumption rates.

Within the range satisfying the above-described conditions, the number of plates in the main column, the column top zone, the column bottom zone, the upper feed zone, the lower feed zone, the upper outflow zone and the lower outflow zone can be adjusted as necessary.

According to one embodiment of the present disclosure, the total column plate number of the main column may be 18 to 70 plates, preferably 20 to 60 plates, and more preferably 20 to 56 plates.

The number of plates in the column top zone may be 5 to 20 plates, preferably 5 to 16 plates, and more preferably 6 to 14 plates. In addition, the number of plates in the column bottom zone may be 5 to 20 plates, preferably 5 to 16 plates, more preferably 6 to 14 plates.

The number of plates in the upper feed zone, the lower feed zone, the upper outflow zone and the lower outflow zone are each independently the same or different and may be 10 to 22 plates, preferably 12 to 20 plates, and more preferably 12 to 18 plates.

According to another embodiment of the present disclosure, there is provided a method for refining vinylidene dichloride comprising the step of fractionally distilling a crude product containing vinylidene dichloride using the dividing wall distillation column.

The dividing wall distillation column used in the method for refining vinylidene dichloride according to the present disclosure is as described above.

Meanwhile, in the refinement method of vinylidene dichloride using the dividing wall distillation column, the content of vinylidene chloride may be about 90% by weight to 99.5% by weight or more, and specifically 99.4% by weight, based on the total weight of the crude product containing vinylidene dichloride.

When the crude product containing vinylidene dichloride is refined using the dividing wall distillation column, vinylidene dichloride can be refined to a purity of at least about 99.5% by weight, preferably at least about 99.7% by weight, more preferably at least about 99.9% by weight.

The operating pressure of the main column may be a static pressure selected in the range of 1 bar to 2 bar, or may vary variably in the above range. In some cases, it may be a static pressure selected in the range of 1 bar to 1.4 bar, or may vary variably in the above range.

The temperature of the column top zone of the main column is preferably 10° C. or more and 45° C. or less at the above pressure.

However, if the temperature of the uppermost plate formed in the column top zone as described above, the vinylidene dichloride contained in the returned liquid stream LD may immediately evaporate, and a phenomenon of flowing out to the condenser drum or polymerizing into polyvinyl chloride may occur.

Therefore, if it is limited to the uppermost plate of the main column, it is preferable that a temperature relatively lower than the temperature range of the column top zone is formed, and the temperature may be formed in the range of 5° C. or more and 10° C. or less.

The temperature of the column bottom zone of the main column is preferably in the range of about 50° C. to about 80° C. at the above pressure. When the temperature is lower than 50° C., the middle boiling component falls to the lower part, and the productivity of the product begins to decrease. When the temperature exceeds 65° C., there is a possibility that the amount of high boiling component flowing out sideways together with a middle boiling component increases, which will deviate from the desired purity of the middle boiling component.

Further, the difference between the temperature of the column top zone and the column bottom zone of the main column may be in the range of about 60° C. or less, for example about 46 to about 50° C.

Even if the temperature difference between the column top zone and the column bottom zone of the main column is within a certain range as described above, due to the design of the optimized distillation column, it is possible to further reduce the energy consumption of the condenser and the reboiler while maintaining high purity of vinylidene chloride and separation efficiency of high boiling components.

The temperature of the crude product of vinylidene dichloride flowed into the feed plates may be about 30 to about 45° C.

When the crude product flows into the dividing wall distillation column of the present disclosure under the inflow conditions as described above to perform the refinement process of vinylidene dichloride, the energy consumption in the reboiler is about 0.460 Gcal/hr or less, for example about 0.390 Gcal/hr to about 0.452 Gcal/h, which can be refined with much lower energy consumption than when using conventional two continuous distillation columns or dividing wall distillation columns having a known construction.

Hereinafter, embodiments of the present disclosure are described in further detail with reference to examples. However, these examples are for illustrative purposes only and are not intended to limit the scope of the present disclosure.

EXPERIMENTAL EXAMPLE 1

Examples 1 to 2

The dividing wall distillation column of the present disclosure was designed and simulated using ASPEN. Two continuous distillation columns without a dividing wall as shown in FIG. 1 were used as Comparative Examples, and a dividing wall distillation column as shown in FIG. 2 was used as Examples.

At this time, the composition of the crude product (hereinafter referred to as the first composition) contained 99.4 wt % of vinylidene dichloride, 0.3 wt % of chloroacetylene as a low boiling component, and 0.3 wt % of cis- and trans-isomers of 1,2-dichloroethene as a high boiling component.

Detailed process conditions of Examples 1 to 2 are shown in Table 1 below, and detailed process conditions of Comparative Example 1 are shown in Table 2 below.

TABLE 1

| | Category | Example 1 | Example 2 |
|---|---|---|---|
| Main column 100 | Column plate nubmer | 35 | 35 |
| Column top zone 20 | Column plate number | 8 | 8 |
| | Temperature and pressure | Pressure: 1.5~2 bar Temperature: 10~45° C. | Pressure: 1~1.4 bar Temperature: 10~35° C. |
| Main column 100 | Inflow condition of crude product | Pressure: 1.5~2 bar Temperature: 30~50° C. Inflow amount: 1000~5000 kg/h | Pressure: 1~1.4 bar Temperature: 30~50° C. Inflow amount: 1000~5000 kg/h |
| | $N1/(N1 + N2)$ | 0.3 | 0.3 |
| Column bottom zone 30 | Column plate number | 8 | 8 |
| | Temperature and pressure | Pressure: 1.5~2 bar Temperature: 60~80° C. | Pressure: 1~1.4 bar Temperature: 50~65° C. |

TABLE 2

| Category | | Condition |
|---|---|---|
| First distillation column 7 | Column plate number | 38 |
| | Inflow condition of crude product | Temperature: 30~50° C. Inflow amount: 1000~5000 kg/h |
| | Column top zone | Pressure: 1~1.9 bar Temperature: 10° C. |
| | Column bottom zone | Pressure: 1~1.9 bar Temperature: 50~60° C. |
| | Reflux ratio | 10~20 |

TABLE 2-continued

| Category | | Condition |
|---|---|---|
| Second distillation column 8 | Column plate number | 26 |
| | Inflow condition of crude product | Temperature: 50~60° C. Inflow amount: 1000~5000 kg/h |
| | Column top zone | Pressure: 1~1.9 bar Temperature: 10~20° C. |
| | Column bottom zone | Pressure: 1~1.9 bar Temperature: 35~50° C. |
| | Reflux ratio | 1~3 |

Under the above conditions, the energy consumed in the processes of Examples 1 and 2 and Comparative Example 1, and the purity of the finally obtained vinylidene dichloride are shown in Table 3 below.

TABLE 3

| | | | Energy consumption |
|---|---|---|---|
| Comparative Example 1 | First distillation column | Reboiler | 0.085 |
| | | Condenser | 0.080 |
| | Second distillation column | Reboiler | 0.441 |
| | | Condenser | 0.409 |
| | Total | | 1.02 |
| | Vinylidene dichloride purity | | 99.9 wt % |
| Example 1 | Reboiler | | 0.452 |
| | Condenser | | 0.435 |
| | Total | | 0.89 |
| | Vinylidene dichloride purity | | 99.9 wt % |
| Example 2 | Reboiler | | 0.399 |
| | Condenser | | 0.393 |
| | Total | | 0.79 |
| | Vinylidene dichloride purity | | 99.9 wt % |

Referring to Table 3, it can be seen that, compared to Comparative Example 1 performing two distillation column processes, the reduction rate of energy consumption of the dividing wall distillation column of the present disclosure is 12.8% (Example 1) and 22.6% (Example 2), respectively, and thus the energy efficiency is significantly improved.

EXPERIMENTAL EXAMPLE 2

Example 3

The process was carried out in the same manner as in Example 1, except that the process was designed such that the quantitative composition ratio in Example 1 satisfies $N1/(N1+N2)=0.5$.

Example 4

The process was carried out in the same manner as in Example 1, except that the process was designed such that the quantitative composition ratio in Example 1 satisfies $N1/(N1+N2)=0.2$.

Comparative Example 2

The process was carried out in the same manner as in Example 1, except that the process was designed such that the quantitative composition ratio in Example 1 satisfies $N1/(N1+N2)=0.1$.

Comparative Example 3

The process was carried out in the same manner as in Example 1, except that the process was designed such that the quantitative composition ratio in Example 1 satisfies N1/(N1+N2)=0.6.

Comparative Example 4

The process was carried out in the same manner as in Example 1, except that the process was designed such that the quantitative composition ratio in Example 1 satisfies N1/(N1+N2)=0.7.

Figure 4:
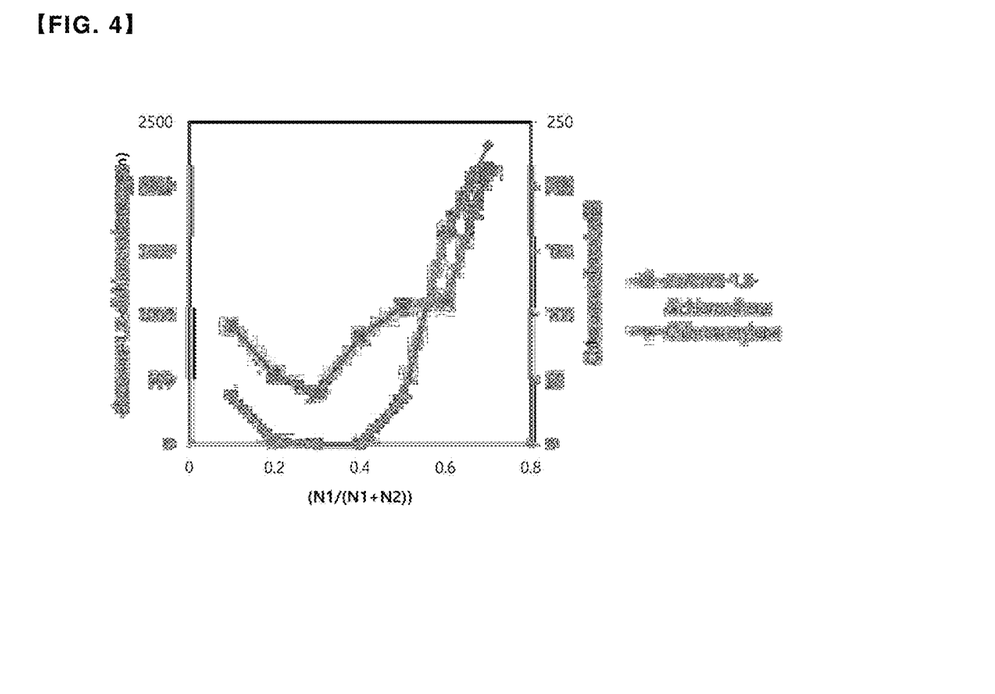
FIG. 4 is a graph showing the results according to Experimental Example 2.

The separation performance of the processes of Examples 1 to 4 and Comparative Examples 2 to 4 were tested under the above conditions, and the results are shown in FIG. 4.

Referring to FIG. 4, it can be seen that in the case of Examples 1 to 4 satisfying the quantitative composition ratio of the present disclosure, the separation efficiency of the cis and trans isomers of chloroacetylene and 1,2-dichloroethane as impurities is excellent and thus, ultra-high purity vinylidene chloride can be obtained. On the other hand, it can be seen that in the case of Comparative Examples 2 to 4 where the process is designed so as to deviate from the quantitative composition ratio of the present disclosure, the content of impurities is very high and thus, vinylidene dichloride is not purified in high purity.

DESCRIPTION OF SYMBOLS

10: dividing wall
10a: first wall
10b: second wall
10c: third wall
20: column top zone
30: column bottom zone
40: feed zone
40a: upper feed zone
40b: lower feed zone
40c: feed plate
50: outflow zone
50a: upper outflow zone
50b: lower outflow zone
50c: outflow plate
100: main column
200: condenser
300: reboiler
400: condenser drum

What is claimed is:

1. A method for refining vinylidene dichloride comprising a step of fractionally distilling a crude product containing vinylidene dichloride using a dividing wall distillation column for fractional distillation of a crude product containing vinylidene dichloride (1,1-dichloroethylene),
  wherein the dividing wall distillation column comprising:
    a main column having a dividing wall, a condenser, and a reboiler,
  wherein the main column includes, based on a vertical cross section, a feed zone and an outflow zone partitioned on one side and the other side, with the dividing wall being interposed therebetween, a column top zone adjacent to an upper end of the dividing wall and a column bottom zone adjacent to a lower end,
  wherein the dividing wall divides a liquid stream into a first stream falling through the feed zone and a second stream falling through the outflow zone, when a liquid stream condensed in the column top zone falls to the column bottom zone, and
  wherein at least a part of the dividing wall is positioned to be deflected in the direction of the feed zone so that a quantitative ratio of the first stream to the second stream satisfies the following Equation 1:

$$N1/(N1+N2)=X \quad (1)$$

wherein, N1 is a flow rate of the first stream, N2 is a flow rate of the second stream, and X is 0.3 to 0.5, and
  wherein the dividing wall includes,
  a first wall adjacent to the column top zone and relatively adjacent to an inner wall of the feed zone on the basis of a virtual vertical plane that symmetrically partitions the main column,
  a second wall adjacent to the column bottom zone and located on the vertical plane, and
  a third wall forming a level difference in an extended form between the first wall and the second wall.

2. The method for refining vinylidene dichloride of claim 1, wherein in the step of fractionally distilling the crude product, an operating pressure of the main column is 1 bar to 2 bar.

3. The method for refining vinylidene dichloride of claim 1, wherein a content of vinylidene dichloride in the crude product is 90% by weight to 99.5% by weight with respect to a total weight of the crude product.

4. The method for refining vinylidene dichloride of claim 1, wherein in the step of fractionally distilling the crude product, a temperature of the column top zone excluding an uppermost plate of the main column is 10° C. or more and 45° C. or less, and
  a temperature of the uppermost plate of the main column is 5° C. or more and 10° C. or less.

5. The method for refining vinylidene dichloride of claim 1, wherein in the step of fractionally distilling the crude product, a temperature of the column bottom zone of the main column is 50° C. or more and 80° C. or less.

* * * * *